(12) United States Patent
Faif et al.

(10) Patent No.: US 8,926,587 B2
(45) Date of Patent: Jan. 6, 2015

(54) PNEUMATIC DEVICE FOR TREATING INTUSSUSCEPTION

(71) Applicants: King Abdullah International Medical Research Center, Riyadh (SA); King Saud Bin Abdulaziz University For Health Sciences, Riyadh (SA); National Guard Health Affairs, Riyadh (SA)

(72) Inventors: Abdulrahman Musa A. Al Faif, Riyadh (SA); Hesham Mohammed Al Shaalan, Riyadh (SA)

(73) Assignees: King Abdullah International Medical Research Center, Riyadh (SA); King Saud Bin Abdulaziz University for Health Sciences, Riyadh (SA); National Guard Health Affairs, Riyadh (SA)

( * ) Notice: Subject to any disclaimer, the term of this patent is extended or adjusted under 35 U.S.C. 154(b) by 0 days.

(21) Appl. No.: 13/769,805

(22) Filed: Feb. 18, 2013

(65) Prior Publication Data

US 2014/0236074 A1    Aug. 21, 2014

(51) Int. Cl.
- *A61M 31/00* (2006.01)
- *A61M 13/00* (2006.01)
- *A61M 16/10* (2006.01)

(52) U.S. Cl.
CPC ......... *A61M 13/003* (2013.01); *A61M 16/1075* (2013.01); *A61M 2202/0225* (2013.01); *A61M 2205/3334* (2013.01); *A61M 2205/3344* (2013.01); *A61M 2205/3368* (2013.01); *A61M 2205/3653* (2013.01); *A61M 2205/581* (2013.01); *A61M 2205/583* (2013.01); *A61M 2205/75* (2013.01)
USPC ................. 604/514; 604/23; 604/26; 604/27; 604/518; 600/560

(58) Field of Classification Search
CPC . A61M 13/003; A61M 31/00; A61M 1/0058; A61M 37/00; A61H 33/14; A61B 17/3747; A61B 17/12022; A61J 15/00; A61F 9/00736
USPC ................. 604/23, 26, 514, 518, 27; 600/560
See application file for complete search history.

(56) References Cited

U.S. PATENT DOCUMENTS

| 5,061,239 A | 10/1991 | Shiels |
| 5,139,478 A * | 8/1992 | Koninckx et al. ............... 604/26 |

(Continued)

FOREIGN PATENT DOCUMENTS

| CN | 2518465 | 10/2002 |
| GB | 2308303 | 6/1997 |

OTHER PUBLICATIONS

R.E. Storey and I.C. Salama, "Design of a Pneumatic Device for Intussusception Reduction in Children", Internet Journal of Third World Medicine, (2004), Vo. 1, No. 2, 8 pages.

(Continued)

*Primary Examiner* — Scott Medway
(74) *Attorney, Agent, or Firm* — Richard C Litman

(57) ABSTRACT

The pneumatic system for intussusception treatment, i.e., invagination of a segment of the intestine into an adjacent segment, includes a pressurized gas supply connected to a series of filters, valves, regulators, and sensors connected to a rectal insertion tube to introduce gas at moderate pressure into the intestine of the patient. A computerized control and monitoring subsystem is included. The system preferably includes a heating system to warm the gas as desired. The system also preferably includes an exhaust portion to relieve internal intestinal pressure as required or desired. The exhaust portion of the system preferably includes a filter to absorb undesirable fecal odors that accompany the exhausted gas. At least the rectal insertion tube and the odor filter may be separable from the remainder of the system for convenient disposal. An alarm may be provided to alert the doctor or medical professional of conditions other than normal.

1 Claim, 2 Drawing Sheets

(56) References Cited

U.S. PATENT DOCUMENTS

| | | | |
|---|---|---|---|
| 5,249,579 A * | 10/1993 | Hobbs et al. | 600/458 |
| 5,328,458 A | 7/1994 | Sekino et al. | |
| 5,549,546 A * | 8/1996 | Schneider et al. | 604/26 |
| 6,203,519 B1 | 3/2001 | Fagerström et al. | |
| 6,299,592 B1 * | 10/2001 | Zander | 604/26 |
| 6,623,453 B1 | 9/2003 | Guibert et al. | |
| 2003/0208223 A1 | 11/2003 | Kleiner | |
| 2006/0149170 A1 * | 7/2006 | Boynton et al. | 601/6 |
| 2008/0269669 A1 * | 10/2008 | Parmigiani | 604/26 |
| 2009/0270794 A1 * | 10/2009 | Mantell | 604/24 |
| 2010/0114011 A1 * | 5/2010 | Herrmann | 604/25 |
| 2010/0150991 A1 * | 6/2010 | Bernstein | 424/447 |
| 2010/0180892 A1 * | 7/2010 | Downie | 128/203.14 |
| 2010/0280489 A1 | 11/2010 | Nishtala et al. | |
| 2011/0082416 A1 | 4/2011 | Iranitalab et al. | |
| 2011/0087160 A1 | 4/2011 | Temple | |

OTHER PUBLICATIONS

J.W. Lee et al., "Intermittent Sonographic Guidance in Air Enemas for Reduction of Childhood Intussusception", J. Ultrasound Med 2006, 25:1125-1130.

* cited by examiner

PNEUMATIC DEVICE FOR TREATING INTUSSUSCEPTION

BACKGROUND OF THE INVENTION

1. Field of the Invention

The present invention relates generally to medical procedures and equipment, and particularly to a pneumatic system for intussusception treatment (the correction of an everted portion of the intestine) that incorporates various pneumatic and computerized components and controls for optimum safety and efficiency.

2. Description of the Related Art

Intussusception is a condition in which a portion of the intestine becomes everted, causing one segment of the bowel to invaginate into a neighboring section so that the bowel commonly appears to have overlapping telescoping sections. The condition is somewhat similar to the telescoping of a larger diameter tube over a tube of smaller diameter. While intussusception is not immediately life threatening, it can be an extremely serious and likely fatal condition if it is left untreated for as little as a few days. This is due to the potential reduction in blood supply to a portion of the affected bowel and resulting necrosis of the tissue, possible bowel perforation or bowel obstruction, and other complications. Intussusception is not common in adults, but is frequently seen in children.

Accordingly, a number of intussusception treatments have been developed in the past. Earlier developed treatments involved invasive surgery to pull the everted portion of the intestine from the normal portion. Later laparoscopic techniques have been developed to accomplish the same goal. Even more recently, the condition has been treated by pressurizing the interior of the intestine using a relatively slight pressure increase over ambient, e.g., 120 mm of mercury (about 2.32 pounds per square inch), using either hydraulic (salt water) or pneumatic (air or other gas) media. The object is not only to expand the intestine diametrically (this is a side effect), but also to cause the intestine to expand its volume by extending longitudinally in the area of the intussusception, thereby causing the everted portion of the intestine to extend from the normal portion to return to a normal condition. The procedure is frequently called an "air enema," and is often performed using a sphygmomanometer attached to a Foley catheter. The results are frequently assessed by ultrasonography, by fluoroscopy, or other radiographic technique. The air enema is quicker than a liquid enema, less messy, and safer if the bowel is perforated.

However, current apparatus for delivering an air enema is generally ad hoc, has insufficient safety measures, and relies upon subjective judgments to determine when the intussusception has been released due to the difficulty of continuous monitoring by sonographic and radiographic techniques.

Thus, a pneumatic system for intussusception treatment solving the aforementioned problems is desired.

SUMMARY OF THE INVENTION

The pneumatic system for intussusception treatment, i.e., the invagination of a segment of the intestine into an adjacent segment, comprises a supply of pressurized gas (air, carbon dioxide, etc.) connected to a series of filters, valves, regulators, and sensors that are, in turn, connected to a rectal insertion tube to introduce gas at moderate pressure into the intestine of the patient being treated for the condition. The system further includes a computerized control and monitoring subsystem to allow the doctor or medical professional to monitor and adjust the various pressure parameters as desired during the treatment.

The system preferably includes a heating system to warm the gas media to normal body temperature, i.e., 37° C. or 98.6° F. The system also preferably includes an exhaust portion to relieve internal intestinal pressure according to the treatment regimen. The exhaust portion of the system preferably includes a filter of activated charcoal or other suitable media to absorb undesirable fecal odors that accompany the exhausted gas. At least the rectal insertion tube and the odor filter may be separable from the remainder of the system for convenient disposal after a single use. The computerized subsystem preferably includes audial and/or visual alarm to alert the doctor or medical professional of conditions other than normal. The pneumatic system may further include a fast acting valve (e.g., solenoid valve, etc.) to produce rapid pressure pulses to produce the desired result if and when such a procedure is deemed desirable by the doctor or medical professional administering the treatment.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The pneumatic system for intussusception treatment provides a non-invasive system for correcting an intussusception disorder, i.e., the invagination of a segment of the intestine into an adjacent segment with accompanying telescoping of the segments. The system is purely pneumatic, and uses no hydraulic fluid. A computerized control and monitoring system is provided with the pneumatic system.

Figure 1:
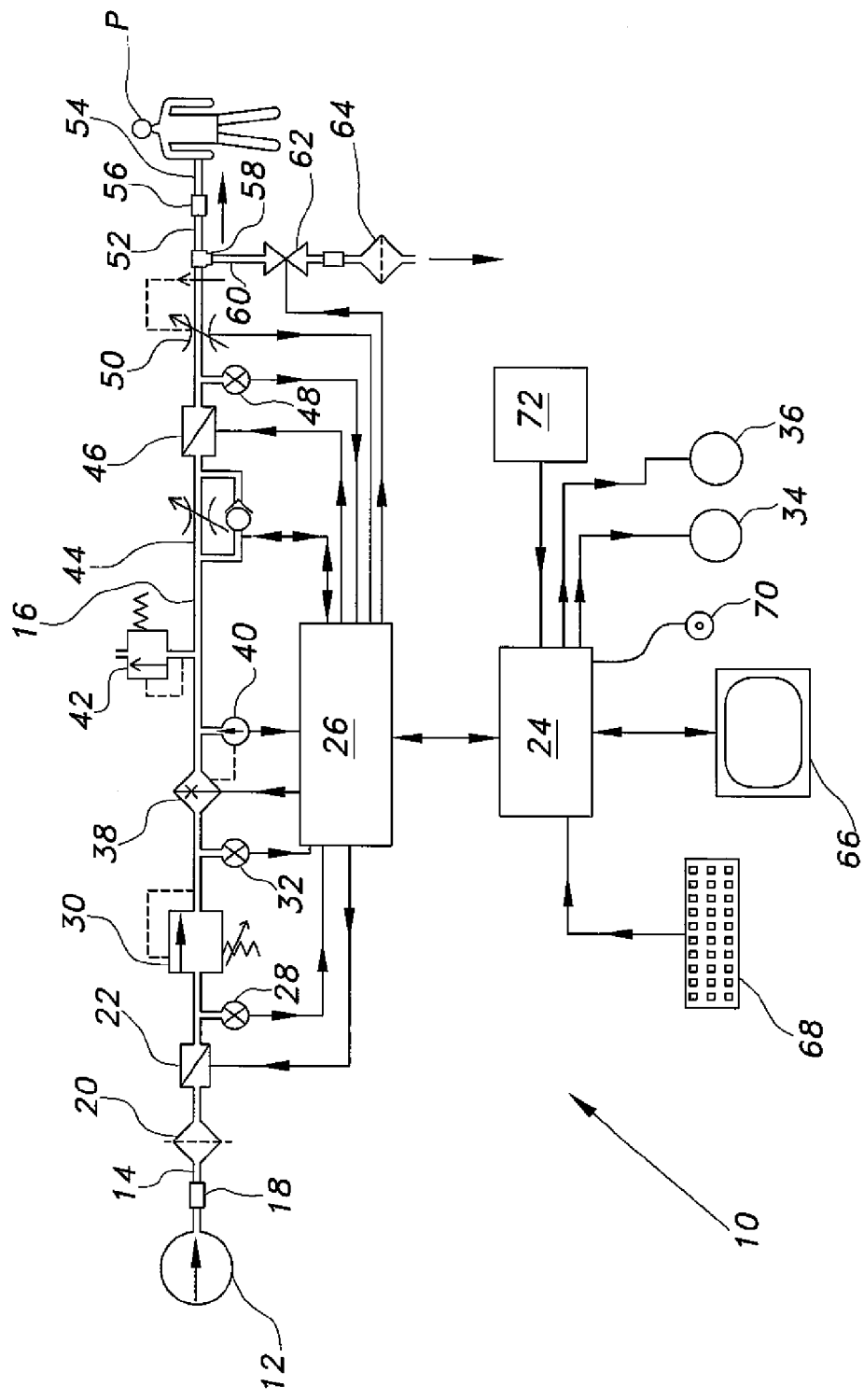
FIG. 1 is a schematic illustration of a pneumatic system for intussusception treatment according to the present invention, showing the various pneumatic and electronic components of the system.

FIG. 1 of the drawings is a schematic view of the combined pneumatic system and computerized control system, generally indicated by the reference numeral 10. The basic system 10 includes a gas supply 12, e.g., a tank of compressed air, carbon dioxide, or other gas. Gas flow is from this gas supply 12 to the left side of FIG. 1, through the various components to the patient P to the right side of FIG. 1. The gas of the gas supply is a non-toxic element, compound, or mixture, and is non-flammable. The gas may be provided under significant pressure, if desired as the system 10 includes one or more pressure regulators therein, as described further below. The gas may be contained in a pressurized tank or other container, or may be provided by a compressor.

The gas supply 12 is connected to the inlet end 14 of a gas supply tube 16 via a disconnect fitting 18 (which may be a conventional quick connect pneumatic fitting), permitting the gas supply 12 to be readily connected to and disconnected from the gas supply tube 16. An inlet filter 20 is preferably installed along the gas supply tube 16 immediately downstream of the inlet end 14 thereof.

A first or primary valve 22, e.g., a solenoid or other suitable shutoff valve, is provided downstream of the inlet filter 20. The valve 22 is normally closed when the system 10 is not in operation, and opens to allow gas to flow from the gas supply 12 through the supply tube 16 during operation of the system. The valve 22 is controlled by a computerized control system comprising a central processing unit (CPU) 24 and interface 26 (e.g., opto-isolators for interfacing high current devices), shown schematically in FIG. 1.

A pressure sensor 28 is installed in the gas supply tube 16 immediately downstream of the primary shutoff valve 22. This sensor 28 communicates electronically with the interface 26, and thus with the CPU 24. The sensor 28 determines the gas pressure developed in the gas supply line 16 by the gas supply 12, and signals the CPU 24 accordingly as described above.

The gas then flows to an automatic pressure regulator 30 installed inline along the gas supply line or tube 16 downstream from the pressure sensor 28. The pressure regulator 30 is set to a predetermined output pressure either manually or under electronic control by the CPU 24, and automatically regulates or modulates the output pressure to the set predetermined output pressure. The regulator 30 reduces the gas pressure in the supply tube 16 to an output of about 120 mm of mercury, or about 2.32 pounds per square inch, above ambient. This pressure is sufficient to produce the desired result in most cases without danger of rupturing the intestine or causing other damage. The components of the system upstream from the pressure regulator 30 may be referred to as the high pressure side of the system 10, and the components downstream of the pressure regulator 30 may be referred to as the low pressure side of the system 10.

The output pressure of the regulator 30 is monitored by a second pressure sensor 32 downstream of the regulator. This second pressure sensor 32 communicates with the CPU 24 through the interface 26 to confirm that the proper output pressure is being provided from the regulator 30. In the event that the regulator 30 fails to reduce the pressure sufficiently, or fails in some other manner, the CPU 24 will provide a signal through the interface 26 to close the first shutoff valve 22 (and/or other valves in the system, described further below) and will send an alarm to an audible alarm 34 and/or visual alarm 36 (either or both may be provided with the system 10).

It is preferred that the gas used in the intussusception treatment be warmed to at least approximately normal body temperature in order to avoid lowering the internal body temperature of the patient and to preclude excessive expansion of the gas due to the body of the patient warming the gas during treatment. Accordingly, a heater 38 is installed along the gas supply tube or line 16 at some point, e.g., downstream of the pressure regulator 30 and pressure sensor 32. The heater 38 is preferably adjusted or set to warm the gas in the supply tube 16 to a temperature of 37° C. or 98.6° F., i.e., normal human body temperature. The output temperature of the heater 38 is preferably adjustable for other temperatures, if desired. A thermostat or temperature sensor and/or controller 40, preferably a closed loop control system using a proportional-integral-derivative (PID) controller) is installed in the gas supply tube or line 16 immediately adjacent to the output end or side of the heater 38. The thermostat or controller 40 communicates with the CPU 24 through the interface 26, and also controls the heater 38. The CPU 24 may be set to send an alarm signal to either or both of the alarms 34 and/or 36 in the event that the temperature output of the heater 38 becomes either too high or too low.

The gas, now warmed and at appropriate pressure, then flows from the heater 38 and thermostat 40 through a relief valve 42. This relief valve 42 functions as a redundant, secondary mechanical safety valve in the event that the pressure output from the regulator 30 exceeds the predetermined maximum and the automated shutdown and release systems fail to function for some reason. The relief valve 42 automatically vents all pressure in the gas supply tube 16 to ambient, in the event of excessive pressure, i.e., that the pressure exceeds 120 mm Hg. As this valve 42 is a mechanical device, it does not necessarily communicate electronically with the CPU 24 and/or interface 26, although it could be connected through the interface 26 and CPU 24 to provide an alarm in the event that it opens.

The warmed and pressure-regulated gas then flows from the outlet side of the relief valve 42 to a mass flow controller 44, which regulates the flow rate of the air or other gas flowing through the supply tube or line 16. The mass flow controller 44 communicates with and is controlled by the CPU 24 through the interface 26. The operator of the system adjusts the gas flow through the mass flow controller 44 as desired by means of the computerized control system.

The system 10 may include a fast acting valve 46 (e.g., solenoid valve or other suitable valve type) installed in line downstream of the mass flow controller 44. This fast acting valve 46 communicates with the CPU 24 through the interface 26 and functions to rapidly change the pressure downstream from the valve 46. The purpose of this function is explained further below. A pressure sensor 48 is installed in the gas supply tube or line 16 downstream from the fast acting valve 46. The sensor 48 also communicates with the CPU 24 through the interface 26. Control of the fast acting valve 46 by the CPU 24 is in accordance with pressure signals provided from the sensor 48.

A flow meter 50 is installed downstream of the fast acting valve 46 and the pressure sensor 48. The flow meter 50 and the pressure sensor 48 provide the operator of the system with real time information (by means of the CPU 24) regarding both the pressure and gas volume measured at the patient P side of the system, the information being displayed graphically on the monitor 66.

A rectal insertion tube 54 is releasably connected to the outlet end 52 of the gas supply tube 16 by an appropriate disconnect fitting 56, which may be similar to the disconnect fitting 18 used to connect the inlet end 14 of the tube 16 to the gas supply 12. The rectal insertion tube 54 is preferably a disposable unit, i.e., configured for single use, although it may be formed of material providing for sterilization and reuse, if desired.

A Tee-fitting 58 is installed in the gas supply tube or line 16 between the flowmeter 50 and the outlet end 52 of the gas supply tube. An exhaust gas tube 60 is releasably attached to the stem of the Tee-fitting 58, and another shutoff valve 62 is installed along the exhaust gas tube 60. The shutoff valve 62 is normally closed during operation of the system 10, in order to maintain the desired pressure and/or flow of gas into the intestine of the patient P by means of the rectal insertion tube 54. The valve 62 is preferably a pinch-type valve, in which a flexible tube or line extends completely through the valve body and is pinched off by a solenoid or other mechanism for closure. This permits the entire exhaust gas tube 60 that passes through the valve 62 to be disposed of after a single use, if desired. The valve 62 communicates electronically with the CPU 24 through the user interface 26. The valve 62 opens and closes on demand in accordance with commands sent from the CPU 24 to control 62, and vary the pressure developed within the system 10 as it is provided to the patient P.

The exhaust gas tube 60 allows excessive gas pressure to be vented from the outlet portion of the system 10, including the mildly pressurized gas that is delivered into the intestine of the patient P. This gas will of course pick up and absorb unpleasant odors that are a normal byproduct of metabolism. Accordingly, an odor filter 64 is installed in line along the exhaust gas tube 60, downstream of the valve 62 and preferably at or adjacent to the outlet end of the exhaust gas tube. The odor filter 64 is preferably an activated charcoal filter, but may be of any suitable type, so long as it does not significantly restrict the gas flow therethrough when the valve 62 is open.

The system 10 is controlled by a human operator through the CPU 24 by means of a visual monitor 66, keyboard or keypad 68, and/or computer mouse 70. The monitor 66 may be a conventional touch screen device, and need not be a full size desktop monitor. A laptop or tablet computer or the like having a suitable monitor may be used. Electrical power for the system and its computerized controls and peripherals is provided by a conventional electrical power supply 72, e.g., from the power grid or other suitable source.

The pneumatic system 10 is operated by initializing power to the computer CPU 24, which provides power to the various valves, controls, heater, etc. of the system through the interface 26. The first solenoid valve 22 in the system is normally closed at this point, with no gas flowing through the supply tube or line 16. The parameters desired (e.g., initial gas flow, maximum pressure, rate of pressure rise, temperature, etc.) are entered into the system by means of the computer 24 and its peripherals. The computer 24 stores these parameters until altered or adjusted by the operator. The system 10 remains in standby mode at this point, i.e., the first solenoid valve 22 remains closed until the system 10 has run its initialization routine and checked the various components for readiness, and until the heater 38 has reached the desired operating temperature. Readiness of the system is indicated on the monitor 66.

At this point, the patient is readied for the procedure (if not previously accomplished), and the rectal insertion tube 54 is inserted into the patient P. The system 10 is then activated and monitored by the operator. The first valve 22 opens at this point, the remaining valves, sensors, controllers, etc. operating in accordance with the programming of the computer 24 and any changes that might be made by the operator during the procedure. The shutoff valve 62 in the exhaust gas tube or line 60 remains closed. The increase in gas pressure within the intestine results in the expansion of the intestine as its internal volume increases. While this causes the diameter of the intestine to increase, it also produces longitudinal pressure along the intestine that results in the release of the intussusception as the intestine expands longitudinally to remove the invaginated section.

Figure 2:
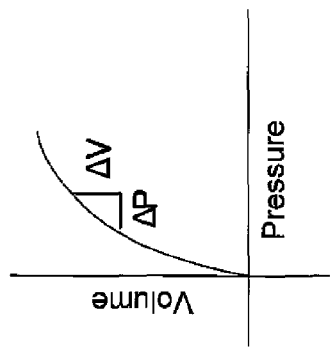
FIG. 2 is a chart showing the relationship between gas pressure and internal volume in the intestine during the operation of the pneumatic system for intussusception treatment according to the present invention.

It will be seen that the volume of the intestine increases proportionally as the internal gas pressure increases, generally in accordance with the graph of FIG. 2. The volume increase $\Delta V$ is initially relatively rapid with the increase in pressure $\Delta P$. The volume increase $\Delta V$ eventually decreases with additional pressure increase, since the compliance of the distended intestine decreases. The gas volume is calculated by integrating the flow rate f, as measured by the flow meter 50, in accordance with the integral $V=\int_{t0}^{t1} f \, dt$. The pressure and volume of gas in the intestine is monitored respectively by the pressure sensor 48 and the flowmeter 50 and transmitted to the computer 24 for monitoring by the operator. A sudden increase in compliance, i.e., a sudden increase in flow measured by the flow meter 50 with either no change or a decrease in pressure measured by the pressure sensor 48, indicates the intussusception has been released. A sudden increase in flow measured by the flow meter 50 accompanied by an increase in pressure measured by the pressure sensor 48 may indicate a leak in the intestine.

As these two components 48 and 50 communicate with the computer or CPU 24, the monitor graphically displays the pressure, the flow rate, and the volume so that the operator may observe such a sudden change in pressure and volume. In addition, the CPU continuously executes a signal processing algorithm to evaluate the instantaneous pressure signals from the pressure sensor 48 and flow readings from the flow meter 50 according to the relationship described in the preceding paragraphs and automatically alerts the operator that the intussusception has been released or that a leak has occurred, either by visual message displayed on the monitor and/or by audio alert.

The system 10 enables the operator to perform additional procedures in the event that the intussusception is not released by the introduction of steadily increasing pressure and volume into the intestine. The operator may direct the system 10 to perform what may be called a "hammer" mode, in which the gas pressure and volume are varied rapidly to pulse compressed air into the intestine. This is accomplished by adjusting the mass flow controller 44 to allow maximum flow and alternately opening and closing the fast acting valve 46 and the pinch valve 62 of the system, i.e., when the fast acting valve 46 is opened the pinch valve 62 is closed to apply pressure, with the fast acting valve 46 then closing and the pinch valve 62 opening to relieve the pressure.

Figure 3:
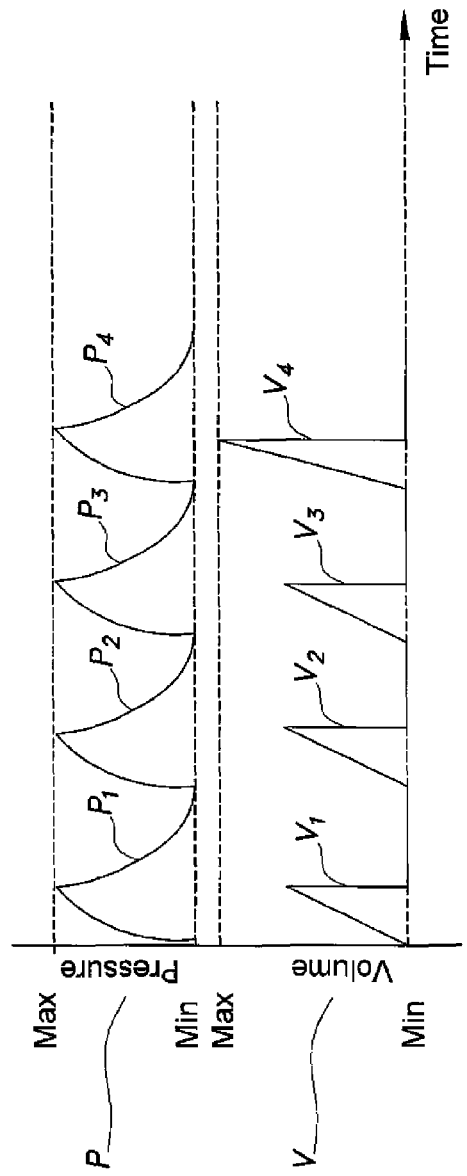
FIG. 3 is a graph of the variation of pressure and volume in the intestine when rapid changes in pressure are used to correct the problem, i.e., a "hammering" mode of operation of the pneumatic system for intussusception treatment according to the present invention.

FIG. 3 of the drawings illustrates a graph showing the rapid variation in both volume (on the lower scale V) and pressure (on the upper scale) over a short span of time. It will be seen that as the pressure increases, as shown by the series of four "sawtooth" pulses $P_1$ through $P_4$ along the upper pressure scale P, the volume increases correspondingly, as shown by the series of volume pulses $V_1$ through $V_4$ along the lower volume scale V. The intestinal volume drops to a constant level between each expansion, as the pressure drops due to the opening of the fast acting valve 46. The graph of FIG. 3 indicates that the intestinal volume increases to a maximum level during each of the first three volume pulses or increases $V_1$ through $V_3$. However, the final volume pulse or increase $V_4$ is somewhat larger than the previous pulses $V_1$ through $V_3$. The only way that this can occur is if the internal volume of the intestine suddenly expands due to the release of the intussusception. Accordingly, the final volume pulse $V_4$ indicates that the intussusception has been released, and no further pressure pulses (and resulting volume increases) are required. The fast acting valve 46 in the gas supply tube or line 16 may then be closed and the shutoff valve 62 in the exhaust gas tube or line 60 opened to relieve all pressure within the intestine of the patient P. The intestinal gas then flows outward through the exhaust gas tube or line 60 and out the odor filter 64. The preferably single use, disposable elements of the system 10, i.e., at least the rectal insertion tube 54, the exhaust gas tube 60 that passes through the pinch valve 62, and the odor filter 64 may be disposed of once the procedure has been completed as described above.

It will be understood that, in use, the system 10 may be used in a single stage approach, setting the output pressure to 120 mm Hg to see if the intussusception can be released by pneumatic treatment. Alternatively, the system 10 may be used in multiple steps, e.g., beginning by setting the output pressure at 60 mm Hg, releasing the gas from the patient's intestine if the intussusception has not been corrected, then increasing the output pressure in 20 mm Hg steps up to 120 mm Hg, so that the intussusception may be corrected using the least amount of pressure required. If the intussusception cannot be released at 120 mm Hg, even with pulsed compressed air in the hammer mode, then surgical invention may be required.

It is to be understood that the present invention is not limited to the embodiments described above, but encompasses any and all embodiments within the scope of the following claims.

We claim:

1. A method for the pneumatic treatment of intussusception, comprising the steps of:
  a) providing a pneumatic intussusception treatment system for maintaining desired pressure and/or flow of gas into the intestine of the patient through a rectal insertion tube intussusception treatment, the intussusception system including:
    i) a gas supply tube having an inlet end and an outlet end opposite the inlet end;
    ii) a supply of pressurized gas selectively connected to the inlet end of the gas supply tube;
    iii) a rectal insertion tube removably connected to the outlet end of the gas supply tube;
    iv) a filter disposed in line along the gas supply tube;
    v) at least one selectively operable valve disposed in line along the gas supply tube;
    vi) at least one pressure sensor disposed in line along the gas supply tube;
    vii) at least one pressure regulator disposed in line along the gas supply tube;
    viii) an exhaust gas tube extending from the gas supply tube adjacent the outlet end thereof;
    ix) a selectively operable valve disposed in the exhaust gas tube;
    x) a computerized control system communicating electronically with the at least one valve and the at least one sensor disposed along the gas supply tube, whereby the desired pressure and/or flow of gas into the intestine of the patient through the rectal insertion tube is maintained; and
    xi) a visual monitor communicating with the computerized control system;
  b) inserting the rectal insertion tube into the patient's rectum;
  c) delivering pressurized gas to the intestines through the rectum; and
  d) maintaining and monitoring the desired pressure and/or flow of gas into the intestine of the patient through the rectal insertion tube until the pressure forces the intestines back to their normal place.

* * * * *